United States Patent [19]
Müller

[11] Patent Number: 4,716,255
[45] Date of Patent: Dec. 29, 1987

[54] PROCESS FOR THE PRODUCTION OF 3,3-DICHLORO-2-METHYLPROPENE

[75] Inventor: Dieter J. Müller, Marl, Fed. Rep. of Germany

[73] Assignee: Huels Aktiengesellschaft, Marl, Fed. Rep. of Germany

[21] Appl. No.: 644,418

[22] Filed: Aug. 27, 1984

[30] Foreign Application Priority Data

Aug. 25, 1983 [DE] Fed. Rep. of Germany ....... 3330610
Apr. 25, 1984 [DE] Fed. Rep. of Germany ....... 3415337

[51] Int. Cl.$^4$ ............................................. C07C 17/06
[52] U.S. Cl. .................................................. 570/216
[58] Field of Search ................................ 570/216, 234

[56] References Cited

U.S. PATENT DOCUMENTS

| 1,235,283 | 7/1917 | Brooks et al. | 570/261 |
| 1,741,305 | 12/1929 | Jaeger | 208/241 |
| 2,189,890 | 2/1940 | Engs et al. | 570/234 |
| 2,284,479 | 5/1942 | Rust et al. | 570/247 |
| 2,302,228 | 10/1942 | Kharash et al. | 562/603 |
| 2,324,249 | 7/1943 | Vaughan et al. | 570/253 |
| 2,380,500 | 7/1945 | Buc et al. | 570/234 |
| 2,411,566 | 10/1946 | Evans | 570/189 |
| 3,405,046 | 10/1965 | Sennewal et al. | 204/158.12 |
| 3,823,195 | 7/1974 | Smith | 570/253 |

FOREIGN PATENT DOCUMENTS 106345  6/1974  German Democratic Rep. ... 73/712

OTHER PUBLICATIONS

Journal of Am. Chem. Soc,. 68:787 (1946).
Journal of Am. Chem. Soc., 61:2145 (1939).
Journal of Am. Chem. Soc., 61:3433 (1939).
Journal of Am. Chem. Soc., 58:1028–1029 (1936).
Journal of Am. Chem. Soc., 69:2614–2616 (1947).
Journal of Am. Chem. Soc., 72:3577 (1950).
Journal of Am. Chem. Soc., 61:3432 (1939).
Brilshen E., III, 1, p. 320 (1958).
B.L. Chem. Soc., Japan 30 (1957), pp. 218–220.
Chem. Abstracts, 33:4190 (1939).
Chem. Abstracts, 63:4148(a)(1965).

Primary Examiner—J. E. Evans
Assistant Examiner—Joseph A. Boska
Attorney, Agent, or Firm—Millen & White

[57] ABSTRACT 3,3-dichloro-2-methylpropene is prepared by reacting 1-chloro-2-methylpropene with sulfuryl chloride in the presence of a catalytically effective amount of nitrogen-containing bases or phosphines. Suitable nitrogen-containing bases are preferably aliphatic, aromatic and heterocyclic amines, as well as mixtures thereof; suitable phosphines are preferably aliphatic or aromatic phosphines.

17 Claims, No Drawings

PROCESS FOR THE PRODUCTION OF 3,3-DICHLORO-2-METHYLPROPENE

BACKGROUND OF THE INVENTION

The present invention concerns a process for the production of 3,3-dichloro-2-methylpropene by reacting 1-chloro-2-methylpropene with sulfuryl chloride.

3,3-dichloro-2-methylpropene is important as an intermediate for organic syntheses on account of its functional groups, namely geminal chlorine substituents as well as a double bond. For example, this product can be used as an intermediate for the preparation of certain Benzofuranes in analogy to EP 0 040 400 which are useful as soil insecticides. Besides that this product can be used itself as a component for insecticides as described in Chem. Abstr. 76 (1972) 122592j.

This product heretofore has not been readily available since it is not obtained, either as a main product or as a by-product, in the industrial gaseous-phase chlorination of isobutene.

Production of 3,3-dichloro-2-methylpropene is possible, with low yield of about 6%, by the introduction of gaseous chlorine, in stoichiometric excess, into boiling 1-chloro-2-methylpropene, under the exclusion of light [A. L. Henne et al., J. Am. Chem. Soc. 72 : 3577 (1950)]. This process is unsuited for an industrially satisfactory manufacture on account of low selectivity.

It is also known that 3,3-dichloro-2-methylpropene can be produced by reacting 1-chloro-2-methylpropene with chlorine in the presence of $NaHCO_3$ in a molar ratio of 1:1:1.5 at 0° C., yielding, besides 68%, 3,3-dichloro-2-methylpropene, 32% 1,1,2-trichloro-2-methylpropane [Chem. Abstr. 33 : 4190 (1939)]. This process is likewise unsatisfactory since it necessitates the use and separation of solid and, moreover, expensive cooling must be provided. The yield is likewise inadequate in this process.

SUMMARY OF THE INVENTION

Accordingly, it is an object of this invention to provide a process for producing 3,3-dichloro-2-methylpropene in a simple way with higher yields.

Upon further study of the specification and appended claims, further objects and advantages of this invention will become apparent to those skilled in the art.

These objects have been attained according to this invention by reacting 1-chloro-2-methylpropene with sulfuryl chloride, in the liquid phase, in the presence of an amine, e.g., a nitrogen base or a phosphine, as catalysts.

DETAILED DISCUSSION

The course of the reaction on which this process is based is entirely surprising:

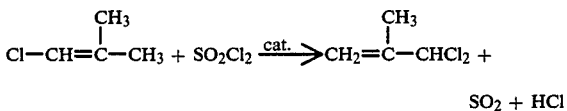

$$Cl-CH=\underset{\underset{CH_3}{|}}{C}-CH_3 + SO_2Cl_2 \xrightarrow{cat.} CH_2=\underset{\underset{CH_3}{|}}{C}-CHCl_2 + SO_2 + HCl$$

Normally, $SO_2Cl_2$ reacts with unsaturated aliphatic compounds either by the addition of chlorine to the double bond and liberation of $SO_2$ or by the addition of the entire molecule to form chloroalkanesulfonic acid chlorides. For example, as is to be expected, 1,2,3-trichloro-2-methylpropane is produced from the isomeric 3-chloro-2-methylpropene with $SO_2Cl_2$ by chlorine addition.

In contrast thereto, in the process of this invention, substitution with simultaneous double bond isomerization takes place as the predominant reaction, if the reaction is conducted in the presence of a nitrogen-containing base, e.g., an amine and/or a phosphine, especially an aliphatic, aromatic, or heterocyclic nitrogen-containing compound or an aliphatic or aromatic phosphine.

The reaction of 1-chloro-2-methylpropene, in the presence of an amine or phosphine, with sulfuryl chloride takes place exothermally with high velocity. It is therefore expedient, for a smooth course of the reaction, to proceed by feeding sulfuryl chloride, with cooling of the reaction mixture, in metered amounts to 1-chloro-2-methylpropene, after having added the amine and/or phosphine and having heated the 1-chloro-2-methylpropene catalyst mixture to a starting temperature of about 30° C. to about 65° C. The rate of addition of $SO_2Cl_2$ is determined by the extent that the sulfuryl chloride is consumed by the reaction. Suitable reaction temperatures of the reaction mixture are up to the boiling point. The removal of the heat of reaction can take place by way of a cooling jacket as well as via an evaporative cooling/reflux condensation system. In accordance with the reaction equation, only the gaseous by-products $SO_2$ and HCl are formed from sulfuryl chloride. These products are continuously released in the gaseous phase from the reaction mixture and removed.

Sulfuryl chloride can be employed in stoichiometric amounts for the reaction. Preferably, an amount of sulfuryl chloride less than the stoichiometric quantity e.g., 65–95% thereof will be used since unreacted 1-chloro-2-methylpropene can be more readily separated from the resultant product than unreacted sulfuryl chloride. Unreacted 1-chloro-2-methylpropene can be reused after separation, so that, in the final analysis, a complete conversion is obtained. However, it is not deleterious to the reaction proper, if $SO_2Cl_2$ is used in stoichiometric excess.

The reaction can be conducted discontinuously, for example in an agitator-equipped reactor, as well as continuously, for example in a tubular reactor or in a cascade. Preferably, the reaction is carried out in the liquid phase.

Suitable nitrogen-containing bases include all N-containing compounds with a free pair of electrons, for example organic compounds including primary, secondary or tertiary amines, e.g., aliphatic amines, such as diisopropylamine, triethylamine, tributylamine (mono-, di- or $tri$-$C_1$-10 - alkyl)amines, or aromatic amines, such as diphenylamine, benzidine or toluidines. or heterocyclic amines, such as pyridine, picolines, pyrrole, pyrazole, quinoline, carbazole or chinaldin. It is also possible to use combinations of several nitrogen-containing bases, the above listing being merely exemplary. Pyridine, picoline, diisopropylamine, triethylamine and/or quinoline are preferably used. But also other than the above mentioned N-containing organic compounds may be useful such as amides like urea resp. substituted ureas or such as hydrazines like diethylhydrazine or even hydrazones.

Normally, a concentration of about 1–10,000 ppm of these compounds is sufficient to catalyze the reaction in the desired way. Preferably, a concentration of 10–1,000 ppm is utilized.

Since chlorinated hydrocarbons in many cases are available already containing added amines as stabilizers, 1-chloro-2-methylpropene, already stabilized in this way, may be reacted in accordance with this invention without requiring the introduction of an additional nitrogen-containing base.

The aliphatic or aromatic (primary, secondary or tertiary) phosphines are normally also employed in a concentration range from 1 to 10,000 ppm, preferably 10–1,000 ppm. Especially suitable are aliphatic phosphines, e.g., those corresponding to the amines disclosed above. Also, the combinations of several phosphines as well as combinations of amines with phosphines are suitable. Aromatic phosphines are also suitable, e.g., those corresponding to the amines discussed above. Triphenylphosphine and/or Tributylphosphin are preferably used. But also other than these P-containing organic compounds may be useful as catalyst such as phosphinoxides like triphenylphosphinoxide or P,P-Dichlorphenylphosphin.

The reaction generally takes place at a temperature of 30°–68° C., preferably 45°–65° C. within a time period of 5 to 200 minutes, preferably 30–120 minutes. The duration of the metered feeding of $SO_2Cl_2$ is, in general, 1–30 minutes, preferably 3–15 minutes. Typically, normal pressure is utilized but suitable pressures include, for example 0.5–3 bar or even higher.

For the isolation of the 3,3-dichloro-2-methylpropene product, the reaction product can be subjected to conventional fractionation. In case of a fractionation carried out at ambient pressures, the fraction having a boiling point of about 108°–112° C. is the desired fraction. Preferably, however, fractionation is conducted under reduced pressure since 3,3-dichloro-2-methylpropene, under thermal stress, tends to rearrange into 1,3-dichloro-2-methylpropene. Pressure conditions should be selected to enable separation of the desired product below 50°–80 ° C.

The yields of 3,3-dichloro-2-methylpropene in the process of this invention generally range above 80%, based on converted 1-chloro-2-methylpropene. The yields vary somewhat with the temperature control, the metering rate of sulfuryl chloride, the choice of catalyst, the reaction time, and the presence of light. Action of light can shift the reaction in the direction toward the production of 1,1,2-trichloro-2-methylpropane. Thus, the reaction is preferably conducted with the exclusion of light. With a suitable selection of parameters, for example at a temperature of 45°–50° C., a metering period of sulfuryl chloride of 1–5 minutes, a reaction time of 60–120 minutes, in the absence of light, yields of above 90% are possible. It is also possible to conduct the reaction in solvents such as $CCl_4$ or other inert diluents.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

An agitator-equipped apparatus with reflux condenser and dropping funnel is charged with 87 g of freshly distilled 1-chloro-2-methylpropene, combined with a nitrogen base as set forth in Table 1, heated to 45° C., and then, in total, 108 g of sulfuryl chloride is added thereto in metered amounts within 3–30 minutes under agitation; the temperature is maintained, by thermostating the agitated flask, in a range of between 45° and about 65° C. The gaseous by-products, $SO_2$ and HCl, formed during the reaction, are withdrawn by way of the reflux condenser and absorbed in a receiver with water rendered alkaline to pH 9.5. The pH value is kept constant by automatic titration with a sodium hydroxide solution of defined concentration, so that the progression of the reaction can be observed with the aid of sodium hydroxide solution consumed. The reaction period ranges between 30 and 180 minutes, depending on the reaction conditions, attaining sulfuryl chloride conversion rates of between 80% and 98%.

The resultant amount of crude product lies between about 115 g and 130 g, depending on reaction conditions. The product is subjected to analysis by gas chromatography after washing with water and drying over $K_2CO_3$. The thus-resulting compositions of pure product can be derived from Table 1; the excess, unreacted 1-chloro-2-methylpropene is eliminated by calculations. The content of desired 3,3-dichloro-2-methylpropene ranges between 80% and 92%.

The test examples have not been optimized with respect to reaction time and yield since they are to demonstrate the course of the reaction, in principle, under the conditions of this invention. It can be seen from the conversion rates of $SO_2Cl_2$, observed by way of titration of thus-formed $SO_2$ and HCl, that especially with pyridine, picoline, diisopropylamine, and triethylamine reaction times of merely 25 minutes are adequate to obtain an above 95% conversion.

TABLE 1

Examples for Reaction of 1-Chloro-2-methylpropene with Sulfuryl Chloride in Less Than Stoichiometric Amount in the Presence of Nitrogen Bases

| Nitrogen Base, Added Amount | ppm | Reaction Temp. °C. | Metered Feeding Time of $SO_2Cl_2$ min | Reaction Period min | Amount of Product g | 3,3-Dichloro-2-methyl-propene | 1,3-Dichloro-2-methyl-propene | 1,1,2-Tri-chloro-2-methyl-propane |
|---|---|---|---|---|---|---|---|---|
| Pyridine | 1,000 | 40–50 | 15 | 60 | 115 | 80.5 | 1.0 | 16.5 |
| Pyridine | 100 | 45 | 30 | 120 | 120 | 84.0 | 1.2 | 11.0 |
| Quinoline | 100 | 45 | 15 | 120 | 121 | 85.0 | 1.3 | 9.5 |
| α-Picoline | 100 | 45 | 10 | 90 | 119 | 84.5 | 1.3 | 10.0 |
| γ-Picoline | 100 | 45 | 10 | 60 | 118 | 87.0 | 0.8 | 8.5 |
| Pyrrole | 1,000 | 45 | 3 | 120 | 121 | 91.5 | 0.5 | 5.5 |
| Pyrazole | 1,000 | 45 | 10 | 180 | 130 | 80.5 | 1.0 | 17.0 |
| Diphenyl-amine | 1,000 | 45 | 10 | 60 | 118 | 81.5 | 1.5 | 15.0 |
| Triethyl-amine | 1,000 | 45 | 10 | 60 | 119 | 80.0 | 1.1 | 15.5 |

TABLE 1-continued

Examples for Reaction of 1-Chloro-2-methylpropene with Sulfuryl Chloride in Less Than Stoichiometric Amount in the Presence of Nitrogen Bases

| Nitrogen Base, Added Amount | ppm | Reaction Temp. °C. | Metered Feeding Time of SO$_2$Cl$_2$ min | Reaction Period min | Amount of Product g | Composition of Pure Product, %* | | |
|---|---|---|---|---|---|---|---|---|
| | | | | | | 3,3-Dichloro-2-methyl-propene | 1,3-Dichloro-2-methyl-propene | 1,1,2-Tri-chloro-2-methyl-propane |
| Diisopropyl-amine | 100 | 45–55 | 15 | 120 | 124 | 80.0 | 1.2 | 16.5 |

*Remainder not identified.

EXAMPLE 2

The process of Example 1 is conducted, but with the difference that initially no nitrogen base is added, and the entire SO$_2$Cl$_2$ is introduced immediately. The reaction is extremely sluggish and even within 60 minutes does not become as vigorous as known from Example 1. After the addition of (a) 0.1% pyridine and (b) 0.1% pyrazole, respectively, the reaction is immediately triggered in the familiar fashion, obtaining the following arrays of products after a reaction period of 180 minutes:

(a) 77.5% 3,3-dichloro-2-methylpropene,
0.5% 1,3-dichloro-2-methylpropene,
18.0% 1,1,2-trichloro-2-methylpropane;
(b) 78.5% 3,3-dichloro-2-methylpropene,
1.0% 1,3-dichloro-2-methylpropene,
18.5% 1,1,2-trichloro-2-methylpropane.

EXAMPLE 3

The procedure of Example 1 is repeated, except that the conversion of SO$_2$Cl$_2$ is controlled quantitatively by titration of the SO$_2$ released in gaseous form along with HCl, after adsorption in aqueous NaOH.

The metered feeding time of sulfuryl chloride is 10 minutes. The nitrogen base selected is 1,000 ppm of triethylamine.

After 10 minutes, i.e. at the end of SO$_2$Cl$_2$ addition, the SO$_2$Cl$_2$ conversion rate is 86%; after 20 minutes, 95%; and after 30 minutes, 97%.

EXAMPLE 4

In the agitator-equipped apparatus described in Example 1, freshly distilled 1-chloro-2-methylpropene is provided, combined with a phosphine according to Table 2, and the process is continued in correspondence with the further description in Example 1.

The results are shown in Table 2.

The preceding examples can be repeated with similar success by substituting the generically or specifically described reactants and/or operating conditions of this invention for those used in the preceding examples. From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the production of 3,3-dichloro-2-methylpropene as predominant product, comprising reacting 1-chloro-2-methylpropene with sulfuryl chloride in the presence of an effective amount of a compatible and nitrogen-containing organic base having a catalytically effective free pair of electrons or phosphine.

2. A process of claim 1, wherein the reaction is carried out in the liquid phase.

3. A process of claim 1, wherein the reaction is carried out under ambient pressure at 30°–68° C.

4. A process of claim 1, wherein the amount of sulfuryl chloride used is less than the stoichiometric amount based on 1-chloro-2-methylpropene.

5. A process of claim 1, wherein the nitrogen-containing base or the phosphine is present in a concentration range from 1 to 10,000 ppm based on 1-chloro-2-methylpropene.

6. A process of claim 1, wherein the catalyst is an aliphatic amine.

7. A process of claim 1, wherein the catalyst is an aromatic amine.

8. A process of claim 1, wherein the catalyst is a heterocyclic amine.

9. A process of claim 2, wherein the catalyst is an aliphatic phosphine.

10. A process of claim 1, wherein the catalyst is an aromatic phosphine.

11. A process of claim 1, wherein the reaction is carried out substantially in the absence of light.

12. A process of claim 3 which is conducted with cooling to maintain said reaction temperature.

13. A process of claim 1, wherein the catalyst is pyridine, a picoline, diisopropylamine, triethylamine or quinoline.

14. A process of claim 1, wherein said concentration range is 10–1000 ppm.

TABLE 2

Example for Reaction of 1-Chloro-2-methylpropene with SO$_2$Cl$_2$ in the Presence of Phosphine

| Phosphine, Added Amount | ppm | Reaction Temp. °C. | Metered Feeding Time of SO$_2$Cl$_2$ min | Reaction Period min | Amount of Crude Product g | Composition of Pure Product, %* | | |
|---|---|---|---|---|---|---|---|---|
| | | | | | | 3,3-Dichloro-2-methyl-propene | 1,3-Dichloro-2-methyl-propene | 1,1,2-Tri-chloro-2-methyl-propane |
| Tributyl-phosphine | 1,000 | 45–50 | 60 | 120 | 117 | 80.5 | 1.0 | 16.0 |
| Triphenyl-phosphine | 1,000 | 45–50 | 60 | 120 | 115 | 75.0 | 2.0 | 21.0 |

*Remainder not identified.

15. A process of claim 1, wherein the reaction temperature is 30°-68° C., the SO$_2$Cl$_2$ is metered into the reaction in 1-30 minutes, and the total reaction time is 50-200 minutes.

16. A process of claim 1 further comprising fractionating the resultant product under reduced pressure.

17. A process of claim 1, wherein the reaction temperature is 45°-50° C., the SO$_2$Cl$_2$ is metered into the reaction in 1-5 minutes and the total reaction time is 60-120 minutes.

* * * * *